United States Patent [19]

Dolhyj et al.

[11] 4,213,917

[45] Jul. 22, 1980

[54] ESTERIFICATION OF AROMATIC ALDEHYDES

[75] Inventors: Serge R. Dolhyj, Parma; Dev D. Suresh, Macedonia; Robert K. Grasselli, Chagrin Falls, all of Ohio

[73] Assignee: Standard Oil Company, Cleveland, Ohio

[21] Appl. No.: 965,653

[22] Filed: Dec. 1, 1978

[51] Int. Cl.$^2$ .............................................. C07C 67/44
[52] U.S. Cl. .......................... 260/465 D; 260/465 R; 260/465 H; 560/77; 560/103; 252/467; 252/468; 252/469; 252/470
[58] Field of Search ............. 260/465 D; 560/77, 103, 560/238; 252/467

[56] References Cited

U.S. PATENT DOCUMENTS

| | | | |
|---|---|---|---|
| 2,198,946 | 4/1940 | Moskovits | 560/103 |
| 3,287,401 | 11/1966 | Pine et al. | 560/238 X |
| 3,584,038 | 6/1971 | Barone et al. | 562/421 X |
| 3,919,305 | 11/1975 | Gay | 560/238 |
| 4,042,533 | 8/1977 | Shaw et al. | 252/469 X |

*Primary Examiner*—Dolph H. Torrence
*Attorney, Agent, or Firm*—W. D. Mooney; Herbert D. Knudsen; Larry W. Evans

[57] ABSTRACT

Aromatic esters are formed directly from aromatic aldehydes by reacting the aldehyde with molecular oxygen and an alcohol in the presence of a heterogeneous molybdenum oxidation catalyst.

32 Claims, No Drawings

ESTERIFICATION OF AROMATIC ALDEHYDES

BACKGROUND OF THE INVENTION

The present invention relates to a novel process for making aromatic esters. More particularly, this invention relates to the catalytic oxidation of an aromatic aldehyde and an alcohol to form an aromatic ester.

The usual method for the preparation of esters is the reaction of a carboxylic acid and an alcohol with the elimination of water. Thus, to make an ester from an aldehyde by prior art methods is a two-step process. In the first step, the aldehyde is oxidized to a carboxylic acid. The acid is then esterified with an alcohol in the second step. A major disadvantage with these processes, however, is that they require two reactors, one reactor to convert the aldehyde to the acid and one reactor to convert the acid to its corresponding ester.

Esters have also been obtained by the condensation of aldehydes in the presence of alcoholate homogeneous catalysts such as aluminum ethylate. The problem with this prior art process is that it is very difficult to separate the homogeneous catalyst from the solvent, reactants and products.

An advantage of the instant invention is that the catalysts are heterogeneous, and thus, can easily be separated from the reactants and products. Furthermore, the instant process results in very high yields, selectivities and conversions to aromatic esters.

SUMMARY OF THE INVENTION

It has now been discovered that aromatic esters can be produced by oxidizing aromatic aldehydes and alcohols over a molybdenum catalyst. For example, it has been found that cyanobenzaldehyde and methanol can be catalytically oxidized to cyanobenzoic acid ester.

Thus, the present invention provides a novel process for the catalytic esterification of aromatic aldehydes by contacting an aromatic aldehyde and an alcohol in air over a catalyt comprising a molybdenum oxide. More specifically, the present invention provides a process for the catalytic esterification of an aromatic aldehyde in which the aromatic aldehyde, the alcohol and molecular oxygen are contacted with a heterogeneous catalyst of the formula:

$$Mo_aX_bY_cO_x$$

wherein
X is one or more elements selected from the group consisting of V, W, Sn, Cu, Sb and P; and
Y is one or more elements selected from the group consisting of Li, Na, K, Rb, Cs, Mg, Ca, Sr, Ba, As, Bi, La, Ce, rare earths, Nb, Ta, Cr, U, Fe, Co, Ni, Zn, Cd, Ag and Tl; and
wherein
a is 0.1–20;
b is 0–4;
c is 0–2;
b+c>0; and
x is the number of oxygens required to satisfy the valence requirements of the other elements present.

In a specific embodiment, the present invention provides a process for the vapor phase catalytic esterification of cyanobenzaldehyde in which cyanobenzaldehyde and methanol are contacted in air with a catalyst comprising an oxide complex of molybdenum and vanadium.

In the case where cyano substituted aromatics are the feed material, it is possible to hydrolyze the cyano group(s) simultaneously with the oxidative esterification of said feed material. Thus, acid-esters, and/or di-esters can be produced. For example, cyanobenzaldehyde can be converted by the process of this invention to di-alkyl-phthalates.

DETAILED DESCRIPTION

Reactants

The instant invention relates to a process for producing an aromatic ester by the catalytic oxidation of an aromatic aldehyde. The overall reaction taking place in this process can be represented by the following equation:

The aromatic aldehyde of the instant invention has the following structure:

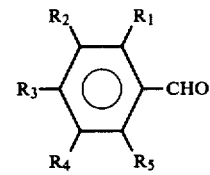

wherein $R_1$, $R_2$, $R_3$, $R_4$ and $R_5$ are each independently selected from the group consisting of:
(1) H;
(2) $(CH_2)_qCN$ wherein q is 0–3;
(3) $C_{1-4}$ alkyl;
(4) $(CH_2)_tCHO$ wherein t is 0–3; and
(5) an aryl group optionally substituted by at least one lower alkyl radical.

Preferably, $R_1$, $R_2$, $R_3$, $R_4$ and $R_5$ are each independently selected from the group consisting of:
(1) H;
(2) $C_{1-3}$ alkyl;
(3) CN; and
(4) CHO.

More preferably $R_1$, $R_2$, $R_3$, $R_4$ and $R_5$ are each independently selected from the group consisting of H, $CH_3$ and CN. Most preferably the aromatic aldehyde used in the inventive process is cyanobenzaldehyde.

The alcohol reactant is represented by the formula: $R_6OH$ wherein $R_6$ is a $C_{1-30}$ linear or branched alkyl. Preferably, $R_6$ is a $C_{1-10}$ linear or branched alkyl and more preferably the alcohol contains 1–4 carbon linear or branched atoms. The most preferred alcohol reactant is methanol.

Any source of molecular oxygen may be employed in the instant process. Air is the preferred source. While the molar ratio of oxygen ($O_2$) to the aromatic aldehyde is not critical to the instant process, the stoichiometric molar ratio of oxygen to aromatic aldehyde is 0.5:1. While the reaction can be accomplished at below or above stoichiometry of $O_2$/aromatic, it is generally preferred to use an excess of oxygen.

It has also been discovered that it may be advantageous to add water to the reaction system. Thus, in one embodiment, an aromatic aldehyde, an alcohol and water are reacted in air to produce the instant aromatic esters.

A wide range of reactant feed ratios are operable in the instant invention. Preferably, the feed ratio of aromatic aldehyde/H$_2$O/alcohol/air will be about 1/0–10-/1–10/2–20.

Any material which is inert to the reactants, catalysts and products of the inventive reaction may also be included in the reaction system as a diluent. For example, steam, nitrogen gas, inert gases, carbon dioxide, water, paraffins and/or benzene could be added to the reaction system, if desired.

Process Conditions

In carrying out the inventive process, the aromatic aldehyde, alcohol and oxygen are contacted with a catalyst as described below for effecting the oxidation process. The inventive reaction can be accomplished both in the batch mode and continuously with both fixed and fluid catalyst beds. The instant reaction can also take place in either the gas phase, liquid phase or a mixed gas/liquid phase.

Reaction temperatures are normally maintained between 150° C. and 600° C., and more preferably 250° C. to 450° C. The reaction pressure is normally maintained at atmospheric pressure but may also be conducted at subatmospheric or superatmospheric pressure. The apparent contact time of the catalyst in the reactants may vary from about 0.1 to 20 seconds for the fixed-bed process, preferably 1 to 5 seconds, and more preferably about 2 seconds. A corresponding contact time is used for fluid-bed processes. In general, lower reaction temperatures require longer contact times and higher reaction temperatures require shorter contact times.

Catalysts

The catalyst employed in the inventive process comprises an oxide or oxide complex. This catalyst can be described by the formula:

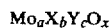

$$Mo_a X_b Y_c O_x$$

wherein
X is one or more elements selected from the group consisting of V, W, Sn, Cu, Sb and P; and
Y is one or more elements selected from the group consisting of Li, Na, K, Rb, Cs, Mg, Ca, Sr, Ba, As, Bi, La, Ce, rare earths, Nb, Ta, Cr, U, Fe, Co, Ni, Zn, Cd, Ag and Tl; and
wherein
a is 0.1–20;
b is 0–4;
c is 0–2;
b+c>0; and
x is the number of oxygens required to satisfy the valence requirements of the other elements present.

The catalyst can be any catalyst delineated by the general formula above with respect to the components of the catalyst. Preferred are those catalysts wherein X is one or more of V, Sb, P and Cu; Y is one or more of La, Ce, Cr, Fe, Co, Ni and Mg; and a is 8–16, b is 0.5–3 and c is 0–1.

The exact chemical nature of the catalyst of the invention is not known. The catalyst may be a mixture of oxides, for example, or an oxide complex of all the contained elements. In any event, this type of catalyst is generally known in the art.

Catalyst compositions similar to those of the present invention are known in the art. For example, the disclosure in U.S. Pat. Nos. 3,567,773, 3,893,951 and 3,956,377 show catalyst compositions containing the elements molybdenum, vanadium and tungsten and the disclosure in U.S. Pat. No. 4,042,533 discloses catalyst compositions containing molybdenum, vanadium, tungsten, rhenium or titanium and one or more optional promoter elements. The catalysts of the invention can be made by techniques which are essentially the same as the techniques described in the above patents, which are herein incorporated by reference. Even though there are numerous preparations which may be utilized to give acceptable catalysts, some of the preferred methods of making the catalysts are described below.

The catalyst of the present invention can be prepared from any mixture of compounds that can be calcined to give the desired oxide component. Preferably, the catalysts are prepared by co-precipitating decomposable salts such as nitrates, acetates, halides and/or oxides to form a catalyst precursor, and then calcining the precursor in the presence of oxygen. Other known catalyst preparation techniques, however, can be employed.

The catalytic activity embodied in the present invention is enhanced by heating the catalysts at elevated temperatures. Preferably, the catalysts are dried and heated at a temperature of about 200° C. to 1000° C., more preferably at about 300° C. to 500° C., for from ½ to 24 hours. If the activity/selectivity relationship is not satisfactory, the catalysts can be further heat treated at a temperature above about 300° C. but below a temperature deleterious to the catalyst.

The catalyst can be in the supported, unsupported or coated form. Preferred support materials are silica, ZrO$_2$, alumina, phosphates, silica-alumina and zeolites. Any other known support material can be used which is stable under the reaction conditions to be encountered in the use of the catalyst. In the supported form, the support preferably comprises 5% to 95% by weight of the catalyst. In the coated catalyst form the inert core material is preferably in the range of from about 20% to 95% by weight of the catalyst.

Recovery

The reaction products obtained upon completion of the reaction are normally in the form of a liquid and gas and composed primarily of aromatic aldehydes, carbon monoxide, carbon dioxide and aromatic esters. This reaction product can be subjected to suitable known separation techniques to yield desired end product, namely the aromatic esters.

For example, the product gas can be condensed and the reaction product separated from any carrier gas that may be in the system. The liquid reaction product can be condensed in an alcohol or acetone trap and can be separated by any suitable separation technique.

There are many known uses for aromatic esters. These esters have a large volume use as carriers in the dyeing of polyester fibers. Also, these esters are used in the field of perfumes, insect repellants, medicinals and plastics. Finally, these esters can be hydrolyzed by known techniques to terephthalic acid.

SPECIFIC EMBODIMENTS

In order to more thoroughly describe the present invention, the following working example is presented. In this example, cyanobenzaldehyde is oxidized in a 40 cc fixed-bed reactor. The gaseous feed is introduced via a calibrated rotometer and the liquid feed is supplied directly into the reactor using a Sage syringe pump. The reactor is heated in a stainless steel block to the desired reaction temperature.

For the purposes of this application, the following definitions are used:

$$\%PPC = \frac{\text{gms. carb. cyanobenzaldehyde conv. to prod.}}{\text{gms. carb. cyanobenzaldehyde fed}} \times 100$$

$$\%Select. = \frac{\text{gms. carb. cyanobenzaldehyde conv. to prod.}}{\text{gms. carb. cyanobenzaldehyde reacted}} \times 100$$

The results have all been adjusted to a 100% carbon balance. The following experiment was conducted:

EXAMPLE 72.0 grams of $MoO_3$ powder, 11.36 grams of $V_2O_5$ powder, 3.13 grams of $SnO_2$ powder and 9.19 grams of tungsten metal powder were added to 750 cc. of distilled $H_2O$. The resultant slurry was stirred under reflux on a hotplate for 2 hours. The color of the slurry changed to dark blue.

16.64 grams of $Cu(acetate)_2.H_2O$ was separately dissolved in 150 cc. of distilled $H_2O$ and added to the above dark blue slurry. This mixture was kept under reflux conditions for an additional ½ hour and then evaporated to a thick black paste. The thick black paste was dried overnight at 110° C. to form a hard black-gray material which has the formmula $Mo_{12}V_3W_{1.2}Sn_{0.5}Cu_2O_x$.

Separately, 25 grams of 10/30 mesh Alundum was pre-wet with 1.09 grams of distilled water in a rotating round glass jar and rolled for 10 minutes until the Alundum surface appeared dry. To the dry appearing Alundum was added five portions, consisting of 1.25 grams each of the catalytically active black-gray material. The catalyst was roller for 10 minutes after each portion was added. The powder coated the Alundum uniformly. Some of the catalytically active black-gray material stuck to the glass walls and had to be scraped off. The Alundum was then rolled for an additional 10 minutes to pick up all the active material. The catalytic material was dried at about 110° C. for 2 hours and activated by calcining it at 400° C. in an atmosphere of air for 2 hours.

The coated catalyst formed had the following composition: 20% $(Mo_{12}V_3W_{1.2}Sn_{0.5}Cu_2O_x)$ 80% Alundum.

The catalyst so obtained was charged into the experimental apparatus described above and a reactant feed having a reactant ratio of 4-cyanobenzaldehyde/methanol/ water/air equal to 1/8/6/10 was then fed to the reactor. The contact time was about 2 seconds and the reactor temperature was 350° C. The liquid reaction product was collected at the reactor exit in two liquid (isopropanol) traps, the second of which was cooled with ice water. The tailgas was analyzed during the run for $O_2$, $N_2$, $CO$ and $CO_2$ using a Carle gas chromatograph. The liquid products, in isopropanol solutions, were analyzed on a Hewlett-Packard gas chromatograph. The results are shown below.

| Product | % PPC |
|---|---|
| $C_6H_5CN$ | 9.8 |
| $C_6H_4(CN)_2$ | 4.3 |
| $CN\phi COOCH_3$ | 15.1 |
| $CH_3OOC\ 100\ COOCH_3$ | 2.6 |

-continued

| Product | % PPC |
|---|---|
| CO | 2.2 |
| $CO_2$ | 4.6 |
| Unreacted 4-cyanobenzaldehyde | 58.4 |
| Selectivity (esters) | 42.6 |

Although only a few embodiments of the present invention have been specifically described above, it should be appreciated that many additions and modifications can be made without departing from the spirit and scope of the invention. These and all other modifications are intended to be included within the scope of the present invention, which is to be limited only by the following claims:

We claim:

1. A process for producing an aromatic ester by the oxidation of an aromatic aldehyde in which the aromatic aldehyde, an alcohol and molecular oxygen are contacted with a catalyst of the formula:

$$Mo_aX_bY_cO_x$$

wherein
X is one or more elements selected from the group consisting of V, W, Sn, Cu, Sb and P; and
Y is one or more elements selected from the group consisting of Li, Na, K, Rb, Cs, Mg, Ca, Sr, Ba, As, Bi, La, Ce, rare earths, Nb, Ta, Cr, U, Fe, Co, Ni, Zn, Cd, Ag and Tl; and wherein
a is 0.1–20;
b is 0–4;
c is 0–2;
b+c>0; and
x is the number of oxygens required to satisfy the valence requirements of the other elements present.

2. The process of claim 1 wherein a is 8–16.
3. The process of claim 2 wherein a is 12.
4. The process of claim 3 wherein b is 1–4 and c is 0.1–3.
5. The process of claim 1 wherein b is 0.5–3.
6. The process of claim 1 wherein c is 0.01–1.
7. The process of claim 1 wherein X is V, Sb, P and Cu or a mixture thereof.
8. The process of claim 6 wherein X is V and Cu or a mixture thereof.
9. The process of claim 7 wherein X is V.
10. The process of claim 1 wherein X=V, W, Sn and Cu or a mixture thereof.
11. The process of claim 1 wherein Y is La, Ce, U, Cr, Fe, Co, Ni and Mg or a mixture thereof.
12. The process of claim 1 wherein the aromatic aldehyde has the following formula:

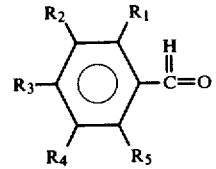

wherein $R_1$, $R_2$, $R_3$, $R_4$ and $R_5$ are each independently selected from the group consisting of:
(1) H;
(2) $(CH_2)_qCN$ wherein q is 0–3;

(3) $C_{1-4}$ alkyl;
(4) $(CH_2)_t CHO$ wherein t is 0–3; and
(5) phenyl.

13. The process of claim 12 wherein $R_1$, $R_2$, $R_3$, $R_4$ and $R_5$ are each independently selected from:
   (1) H;
   (2) $C_{1-3}$ alkyl;
   (3) CN; and
   (4) CHO.

14. The process of claim 13 wherein $R_1$, $R_2$, $R_3$, $R_4$ and $R_5$ are each independently selected from H, $CH_3$, and CN.

15. The process of claim 1 wherein the aromatic aldehyde is cyanobenzaldehyde.

16. The process of claim 1 wherein the alcohol has the following formula:

$$R_6OH$$

wherein $R_6$ is a $C_{1-30}$ linear or branched alkyl.

17. The process of claim 16 wherein $R_6$ is a $C_{1-10}$ linear or branched alkyl.

18. The process of claim 17 wherein $R_6$ is a $C_{1-4}$ linear or branched alkyl.

19. The process of claim 1 wherein the alcohol is methanol.

20. The process of claim 1 wherein the ratio of aromatic aldehyde/alcohol/air is 1/1–10/2–20.

21. The process of claim 18 wherein 0.1–10 moles of water are added to said process per mole of aromatic aldehyde.

22. The process of claim 1 wherein said process is conducted at 150° C. to 600° C.

23. The process of claim 20 wherein said process is conducted at 250° C. to 450° C.

24. The process of claim 1 wherein said process is conducted in the gas phase.

25. The process of claim 1 wherein said process is conducted in mixed liquid/vapor phase.

26. The process of claim 1 wherein said catalyst is supported on a catalyst support.

27. The process of claim 23 wherein the support is selected from the group consisting of silica, alumina, zirconia, silica-alumina, phosphates and zeolites.

28. The process of claim 1 wherein said catalyst is in a coated form.

29. The process of claim 1 wherein b is greater than 0.

30. The process of claim 1 wherein c is greater than 0.

31. The process of claim 1 wherein both b and c are greater than 0.

32. The process of claim 1 wherein said catalyst is substantially free of rhenium and titanium.

* * * * *